United States Patent [19]

Günther et al.

[11] Patent Number: 4,622,301

[45] Date of Patent: Nov. 11, 1986

[54] 2-OXOCARBOXYLIC ACID REDUCTASE AND ITS PREPARATION

[75] Inventors: Helmut Günther, Haag; Stefan Neumann, Eching; Helmut Simon, Freising, all of Fed. Rep. of Germany

[73] Assignee: BASF Aktiengesellschaft, Ludwigshafen, Fed. Rep. of Germany

[21] Appl. No.: 648,043

[22] Filed: Sep. 7, 1984

[30] Foreign Application Priority Data

Sep. 9, 1983 [DE] Fed. Rep. of Germany ....... 3332562

[51] Int. Cl.$^4$ .......................... C12P 7/42; C12P 7/62; C12N 9/02; C12R 1/37
[52] U.S. Cl. ................................... 435/146; 435/135; 435/189; 435/873
[58] Field of Search ............... 435/189, 190, 135, 139, 435/146, 280

[56] References Cited

U.S. PATENT DOCUMENTS 4,020,036 4/1977 South, Jr. .............................. 260/40
4,035,438 7/1977 Nielinger et al. ................... 260/857
4,530,903 7/1985 Leuchtenberger et al. ........ 435/130

FOREIGN PATENT DOCUMENTS 1015236 12/1965 United Kingdom .

OTHER PUBLICATIONS

Journal of Organic Chemistry, vol. 47, pp. 2816–2818 (1982).
Applied & Environmental Microbiology (1983), pp. 884–891.
De Ley: "2-Ketogluconic Acid Reductase", in Methods in Enzymology, vol. IX, pp. 196–200.
Kohn et al.: "Hydroxypyruvate Reductase", in Methods in Enzymology, vol. IX, pp. 229–232.

Primary Examiner—Lionel M. Shapiro
Attorney, Agent, or Firm—Keil & Weinkauf

[57] ABSTRACT

A novel enzyme for the reduction of 2-oxocarboxylic acids, and its preparation, are described.

3 Claims, No Drawings

2-OXOCARBOXYLIC ACID-REDUCTASE AND ITS PREPARATION

The present invention relates to a noveL 2-oxocarboxylic acid reductase, its preparation and its use for the reduction of 2-oxocarboxylic acids.

It is known that 2-oxocarboxylic acids can be reduced enzymatically. These reductions are carried out using enzymes which require pyridine nucleotides as cosubstrates. An example of such a reaction is the preparation of an L-lactate from a pyruvate (J. Org. Chem. 47 (1982), 2816). It has also been disclosed that optically pure 2-hydroxycarboxylic acids can be prepared from racemic mixtures of 2-hydroxycarboxylic acids by enantioselective microbial degradation (Appl. Environ. Microbiol. 45 (1983), 884). However, the enzymatic reduction with reductases which are dependent on pyridine nucleotides has the disadvantage that a second enzyme is required in order to regenerate the oxidized pyridine nucleotide. Moreover, the pyridine nucleotides decompose on prolonged use.

We have found an enzyme which does not have these disadvantages.

The present invention relates to a 2-oxocarboxylic acid reductase which is independent of pyridine nucleotides and does not contain any flavine groups.

The oxocarboxylic acid reductase has a molecular weight of about 500,000 and an isoelectric point of 4.9, and can be used within a pH range from 6 to 8, the optimum pH being 6.8. The temperature dependence of the activity of the enzyme is shown in the table below, the reference value being the activity at 24° C., which has been taken as 100%.

TABLE 1

| T (°C.) | Activity (%) | T (°C.) | Activity (%) |
|---|---|---|---|
| 14 | 46 | 34 | 220 |
| 19 | 72 | 39 | 306 |
| 24 | = 100 | 44 | 368 |
| 29 | 150 | 49 | 440 |

At 45° C., the oxidized enzyme in a phosphate buffer in the presence of tetracyclin has a half-life of about 13 hours. At 35° C., this time is about 55 hours, and in the reduced state in the presence of reduced methylviologen, it is about 100 hours. The activity does not exhibit a first order curve. After 8 hours and 40 hours, no decrease in activity is observed in the case of the oxidized enzyme. The activity of the enzyme is not affected by EDTA.

The only prosthetic grdup which it has been possible to detect hitherto is acid-labile sulfur, which is presumably derived from Fe/S clusters. Flavine groups cannot be detected by spectrophotometry.

A particularly important feature is the fact that the activity of the enzyme can be increased by oxidized methylviologen. In the presence of increasing concentrations of $MV^{++}$ and 0.15 mM $MV^+$, the initial rates show the following behavior:

| $MV^{++}$ mM | U/ml P. mirabilis | P. vulagris |
|---|---|---|
| 0.01 | 18.1 | 13.3 |
| 0.08 | 41.9 | 24.4 |
| 0.16 | 46.0 | 31.3 |
| 0.75 | 62.0 | 41.5 |

(0.3 ml of 0.1M trisacetate buffer of pH 7.0, 2 μmole of 2-oxo-4-methylpentanoate, the same amount of enzyme in each case, 0.2 mM of reduced methylviologen and the concentrations of oxidized methylviologen stated in the table were incubated in a 2 mm cell.)

The 2-oxocarboxylic acid reductase is obtained by a method in which a microorganism, eg. Proteus vulgaris DSM 30 118 or Proteus mirabilis DSM 30 115, which contains the enzyme is disintegrated mechanically and centrifuged, the supernatant liquid is ultracentrifuged, the sediment is suspended in a detergent solution, and solid impurities are removed by further ultracentrifuging.

The first centrifuging step serves to remove coarse impurities. As a rule, it is carried out at from 5,000 to 20,000 g for from 5 to 10 minutes, and the sediment is discarded. The supernatant liquid is then centrifuged at from 0° to 10° C. and from 80,000 to 120,000 g for from 1 to 2 hours. The resulting sediment is suspended in a cold buffer, and the suspension is once again centrifuged at from 80,000 to 120,000 g. A dispersant, such as Triton ®X 100 or Tween ®80, and a buffer (pH 6–8) are added to the sediment, and the mixture is once again centrifuged at from 80,000 to 120,000 g. The resulting supernatant liquid contains the enzyme in solution.

Surprisingly, the novel enzyme can be used to reduce a large number of 2-oxocarboxylic acids and their esters stereospecifically to the corresponding (2R)-hydroxycarboxylic acids and their esters. Examples of such acids are 2-oxopropionic acid (=pyruvic acid), 3-fluoro-2-oxopropionic acid, 3-methyl-2-oxopentanoic acid (both enantiomeric forms), 4-methyl-2-oxopentanoic acid, phenyl ketoacetic acid, phenylpyruvic acid, 5-benzyloxy-β-indolylpyruvic acid, ketosuccinic acid, 2-oxoglutaric acid, 2-oxoadipic acid, 2-oxoazelaic acid, 2-oxosebacic acid, 2-oxoundecanedicarboxylic acid, 2-oxo-4-(methylthio)-butyric acid, indolylpyruvic acid and 2-oxo-4-methylphosphinobutyric acid. An example of an ester is ethyl pyruvate. As a rule, the optical purity of the reduction products is above 98%, and in some cases is even above 99.5%.

Moreover, the activity of the novel enzyme does not depend on the presence of any reduced pyridine nucleotides. It can transfer electrons directly from an electron carrier, such as methyl- or benzylviologen in the reduced state, onto the substrate.

EXAMPLE 1

Proteus mirabilis (DSM 30 115) was cultured in a complete medium (5.0 g of yeast extract, 5.0 g of glucose, 20.0 g of peptone from meat, 5.0 g of $K_2HPO_4$ and $H_2O$ to make the medium up to 1000 ml; pH 7.2) at 35° C. while gassing with a mixture of 97% of $N_2$ and 3% of $O_2$. Proteus vulgaris (DSM 30118) showed higher enzyme activities in the crude extract. In this case, however, culture must be carried out in the complete absence of oxygen. The crude extract showed specific enzyme activities of 7–9 U/mg of protein. The cells thus obtained were harvested early in the steady-state phase. 1 part by weight of the moist mass of bacteria was suspended in 3 parts of 20 mM potassium phosphate buffer at pH 7.0, and the suspension was placed in an ice bath under an $N_2$ atmosphere and treated in an ultrasonic apparatus until more than 90% of the cells had disintegrated; this was established by means of a microscope.

64 ml of the resulting crude extract were centrifuged for 10 minutes at 10,000 g and 4° C., and the sediment was discarded. The supernatant liquid was centrifuged for 90 minutes at 100,000 g and 4° C., and the supernatant liquid was discarded. The sediment was washed with 32 ml of 20 mM potassium phosphate buffer at pH 7.0, and once again centrifuged for 60 minutes at 100,000 g, the supernatant liquid once again being discarded. The sediment was suspended in 32 ml of 20 mM potassium phosphate buffer at pH 7.0, which contained 0.2 g of Triton ®X 100. The suspension was stirred for 45 minutes and then centrifuged for 60 minutes at 100,000 g and 0° C. The reductase was present in the supernatant liquid, and the yield was 80%.

EXAMPLE 2

10 ml of the crude extract obtained as described in Example 1 and having a total activity of 300 U (specific activity 1.3 U/mg of protein) were introduced onto a Sephacryl ® S-1000 column (bed volume 425 ml), and were eluted with 20 mM potassium phosphate buffer at pH 7.0, at 4° C., using a flow rate of 30 ml/hour. The enzyme appeared in conjunction with membrane particles after about 6 hours. The active fractions (55 ml) were combined, and concentrated to 7 ml by ultrafiltration.

This 7 ml portion contained 90% of the enzyme of the crude extract, with a specific activity of 24 U/mg.

EXAMPLE 3

50 g of a moist mass of bacteria were disintegrated by a method similar to that described in Example 1. The volume of the supernatant liquid from the final centrifuging step was concentrated to 11 ml by ultrafiltration (500 U/ml of reductase and 37 mg of protein per ml), and was then introduced onto a Sepharose ® 6B column (volume 440 ml) and eluted with a solution of 20 mM potassium phosphate buffer at pH 7.0, 0.05% of Triton ® X 100 and 1 mM of dithioerythritol. The combined enzyme-containing fractions were concentrated to 35 ml by ultrafiltration. Dilution followed by repeated ultrafiltration gave 35 ml of a solution which was 10 mM with respect to potassium phosphate buffer. The solution was introduced onto a hydroxyapatite column (Bio Gel HTP) which had a bed volume of 100 ml and was equilibrated with 10 mM phosphate buffer, 0.05% of Triton ® X 100 and 1 mM dithioerythritol, after which elution was carried out using a linear gradient of 10–100 mM phosphate buffer and the additives stated above. The combined enzyme-containing fractions were concentrated to 50 ml by ultrafiltration, this volume containing 0.37 mg of protein per ml and 26 U/ML of a reductace. After dialysis for 9 hours against 10 mM tris.HCl at pH 7.5 and 0.05% of Triton X 100, the enzyme solution was introduced onto a DEAE-Sephadex ® A25 column having a bed volume of 35 ml, and the enzyme was eluted using a linear gradient of 0–700 mM KCl in the above buffer. Concentration of the combined enzyme-containing fractions to 8.2 ml by ultrafiltration gave a specific activity of 300 U/mg of protein (90 U/ml; 0.3 mg of protein per ml).

EXAMPLE 4

40 g of a moist mass of Proteus vulgaris bacteria were suspended in 60 ml of 0.01 M tris.HCl buffer at pH 7.5 and 1 mM of dithioerythritol, and the suspension was disintegrated by means of ultrasonic treatment (30 min, 40 watt, temperature no higher than 6° C). The lysate was centrifuged for 10 minutes at 15,000 g, and the supernatant liquid for 120 minutes at 100,000 g. The sediment was resuspended in 75 ml of 0.01 M tris.HCl buffer at pH 7.5, and 1% (v/v) of detergent (polyoxoethylene-9-lauryl ether (Sigma)) was added. This suspension was stirred for 45 minutes in an ice bath, after which centrifuging was once again carried out at 100,000 g for 90 minutes. The supernatant liquid contained the 2-oxocarboxylic acid reductase.

The solution was introduced onto a DEAE cellulose column which had a diameter of 2.5 cm and a volume of 90 ml and had been equilibrated with 0.1 M tris.HCl at pH 7.5, 1 mM dithioerythritol, 0.8% (v/v) of detergent and 4 mM of dithionite. Elution was carried out using about 2 column volumes of the above buffer, after which a linear gradient of 0.1–0.7 M KCl ($2 \times 225$ ml) in the above buffer was employed. The enzyme was eluted at about 250 mM KCl, and was present in a volume of about 60 ml. The enzyme-containing fractions were combined and then introduced onto a hydroxyapatite column (HA Bio-Gel) which had a diameter of 1.5 cm and a volume of 40 ml and had been equilibrated with 0.01 M tris.HCl at pH 7.5, 1 mM dithioerythritol, 0.4% (v/v) of detergent and 4 mM of dithionite. When elution with the above equilibration buffer was complete (about 1 column volume), elution was carried out using a linear gradient of 0–150 mM potassium phosphate at pH 7.5 and the abovementioned additives, the enzyme being obtained at about 60 mM potassium phosphate buffer. The combined fractions (about 30 ml) were introduced onto a second DEAE cellulose column which had a diameter of 1 cm and a volume of 20 ml and had been equilibrated with the above buffer. After further elution for a short time, the 2-oxocarboxylic acid reductase was eluted using a linear gradient of 0–0.4 M KCl once again in the above buffer. The enzyme-containing fractions possessing the principal activity were combined, and were concentrated to about 6 ml by ultrafiltration over a YM 30 membrane (Amicon). This solution was chromatographed over a Sepharose Cl 6B column which had a diameter of 2.5 cm and a volume of 365 ml and had been equilibrated with 0.01 M tris.HCl buffer at pH 7.5, 0.05 M KCl and the abovementioned additives. The enzyme showed a specific activity of 350 U/mg of protein. The purification procedure is shown in the attached table.

| | | | | Concentrating 2-oxocarboxylate reductase | | | | |
|---|---|---|---|---|---|---|---|---|
| Concentration step | Volume V [ml] | Total amount of protein $M_{Pr}$ [mg] | Protein concentration $c_{Pr}$ [mg/ml] | Activity per unit volume VA [U/ml] | Total activity TA [U] | Specific activity SA [U/mg] | N-fold concentration | Yield in % |
| Crude extract | 90 | 1750 | 19.4 | 55 | 5000 | 2.8 | — | 100 |
| Solubilized enzyme | 80 | 560 | 7 | 50 | 4000 | 7.2 | 2.6 | 80 substantially $H_2$ ase-free |
| After DEAE cellulose I | 55 | 248 | 4.5 | 54.5 | 3000 | 12 | 4.3 | 60 $H_2$ ase-free |
| After hydroxy-apatite | 40 | 68 | 1.7 | 48 | 1950 | 28.5 | 10.2 | 39 |

-continued

| | Concentrating 2-oxocarboxylate reductase | | | | | | | |
|---|---|---|---|---|---|---|---|---|
| Concentration step | Volume V [ml] | Total amount of protein $M_{Pr}$ [mg] | Protein concentration $c_{Pr}$ [mg/ml] | Activity per unit volume VA [U/ml] | Total activity TA [U] | Specific activity SA [U/mg] | N-fold concentration | Yield in % |
| After DEAE cellulose II and ultrafiltration | 6.6 | 10.4 | 1.58 | 166 | 1100 | 105 | 37.5 | 22 |
| After Sepharose CL 6B and ultrafiltration | 3 | 1.86 | 0.62 | 220 | 660 | 350 | 125 | 13.2 |

EXAMPLE 5

In an electrochemical cell, 25 ml of a solution of 100 mM potassium phosphate buffer at pH 7.0, 4 mM methylviologen and 40 mM phenylpyruvate were reduced with 0.5 mg of 2-oxoacid reductase according to Example 3 at a voltage of −700 mV, against a standard calomel electrode. The current of 5.8 mA decreased sharply after 9 hours. According to HPLC analysis, the reaction solution contained 88% of the phenyllactic acid expected. The solution was acidified to pH 1.8 with dilute sulfuric acid and then extracted with ether. The crystalline residue (78% of theory) was converted to the sodium salt, which had a specific rotation of $[\alpha]^{RT}589=21.1°$ (0.09 millimole/ml of $H_2O$). A pure commercial preparation of (2S)-sodium phenyllactate gave a value of −21.4°, measured under the same conditions. (R)-mandelic acid and (R)-2-hydroxy-4-methylpentanoate were prepared by a similar method.

Table 2 below shows the relative rates of reduction of the 2-oxocarboxylic acids, the rate for phenylpyruvate being taken as 1. 3-Oxocarboxylic acids and hydroxyacetone are not reduced.

TABLE 2

| | Relative rates | |
|---|---|---|
| Substrate | P. mirabilis | P. vulgaris |
| Phenylpyruvate | = 1.00 | = 1.00 |
| Pyruvate | 0.92 | 0.85 |

TABLE 2-continued

| | Relative rates | |
|---|---|---|
| Substrate | P. mirabilis | P. vulgaris |
| Oxalacetate | 0.73 | 0.50 |
| 2-Oxoglutarate | 0.78 | 0.62 |
| 2-Oxoadipate | 0.70 | |
| Indolylpyruvate | 0.35 | 0.67 |
| 5-Benzyloxyindolylpyruvate | 0.30 | |
| 2-Oxopantoate | 0.07 | 0.04 |
| 3-Fluoropyruvate | 0.22 | 0.20 |
| 2-Oxo-4-methylpentanoate | 0.81 | |
| (+) 2-Oxo-3-methylpentanoate | 0.28 | 0.25 |
| (±) 2-Oxo-3-methylpentanoate | | 0.46 |
| Phenylglyoxylate | 0.16 | 0.05 |
| 3-Oxoglutarate | 0 | |
| Hydroxyacetone | 0 | |

We claim:

1. A 2-oxycarboxylic acid reductase which is independent of pyridine nucleotides, has a molecular weight of about 500,000, an isoelectric point of 4.9 and can be used within the pH range from 6 to 8, the optimum pH being 6.8 and which does not contain any flavine groups.

2. A process for the preparation of a 2-oxocarboxylic acid reductase as claimed in claim 1, wherein a proteus microorganism containing the enzyme is disintegrated, the crude extract is centrifuged, the supernatant liquid is ultracentrifuged, the sediment is suspended in a detergent solution, and solid impurities are removed by further ultracentrifuging.

3. A process for the reduction of a 2-oxocarboxylic acid or its esters, using a 2-oxocarboxylic acid reductase as claimed in claim 1.

* * * * *